United States Patent [19]

Sireul et al.

[11] Patent Number: 4,923,295

[45] Date of Patent: May 8, 1990

[54] DEVICE TO MONITOR A PATIENT IN AN APPARATUS FOR MEDICAL EXAMINATION

[75] Inventors: Jacques Sireul, Wissous; Jacob Hervé, Cugnaux; Gauthier René, Antony, all of France

[73] Assignee: General Electric CGR SA, Paris, France

[21] Appl. No.: 281,011

[22] Filed: Dec. 7, 1988

[30] Foreign Application Priority Data

Dec. 8, 1987 [FR] France ................................ 87 17052

[51] Int. Cl.$^5$ .................................................. G02C 5/08
[52] U.S. Cl. .................................... 350/639; 350/626; 128/653 A
[58] Field of Search ...................... 350/626, 632, 639; 128/653 A, 653 SC

[56] References Cited

U.S. PATENT DOCUMENTS

| | | |
|---|---|---|
| 3,906,953 | 9/1975 | Wallace et al. . |
| 4,531,813 | 7/1985 | Van den Berg .................... 350/632 |
| 4,650,299 | 3/1987 | Stevens et al. . |
| 4,675,888 | 6/1987 | Gastrin ................................. 378/40 |
| 4,804,261 | 2/1989 | Uirshen ................................ 351/50 |

FOREIGN PATENT DOCUMENTS

| | | |
|---|---|---|
| 0125808 | 11/1984 | European Pat. Off. . |
| 0145892 | 10/1984 | PCT Int'l Appl. . |
| 84/04876 | 12/1984 | PCT Int'l Appl. . |

Primary Examiner—Bruce Y. Arnold
Assistant Examiner—Jay Patrick Ryan
Attorney, Agent, or Firm—Oblon, Spivak, McClelland, Maier & Neustadt

[57] ABSTRACT

A device for monitoring a patient in a medical examination apparatus has a support on which are mounted a television camera and a mirror sending on an image of a part of the patient to the camera, said support being movable with respect to the frame of the apparatus but fixed with respect to the patient.

12 Claims, 4 Drawing Sheets

DEVICE TO MONITOR A PATIENT IN AN APPARATUS FOR MEDICAL EXAMINATION

BACKGROUND OF THE INVENTION

1. Field of the Invention

The present invention concerns a device to monitor a patient in an apparatus used for medical examinations. More particularly, it concerns a device to monitor a patient in an apparatus for imaging by nuclear magnetic resonance (NMR) or similar type of apparatus.

2. Description of the Prior Art

In an apparatus for imaging by nuclear magnetic resonance, the patient lies down, during the examination, inside a tunnel formed by the different magnets creating the magnetic field, this tunnel being itself surrounded by a Faraday cage. The patient is therefore in a rather claustrophobic environment. To increase the patient's comfort, it is therefore preferable to ventilate and illuminate the examination tunnel and to be able to converse with the patient. Because of this, the patient is linked to the operator by a system of loudspeakers and microphones, as well as by a manually-operated distress signal system. In any case, the patient has to be constantly monitored so that any anomaly in his behaviour can be detected. To do this monitoring, there are television camera systems connected to a monitoring display screen implanted in the operator's control desk. This television camera cannot be positioned fixedly inside the examination tunnel because, the patient is not always placed in the same position during the examination: this position depends on the part of the body which has to be examined. To enable fool-proof detection of any anomalies in the patient's behaviour, the main zones that have to be observed are, particularly, the mouth and the eyes. Now, currently used monitoring devices do not enable these zones to be detected irrespectively of the patient's position inside the examination tunnel.

It is an object of the present invention to cope with these drawbacks by proposing a device to monitor the patient in a medical examination apparatus, enabling the patient to be monitored irrespectively of his position inside the examination tunnel.

Another object of the present invention is to provide a device to monitor the patient in a medical examining apparatus, where this monitoring device is set once and for all and accepts all possible configurations of examination.

SUMMARY OF THE INVENTION

Consequently, an object of the present invention is a device to monitor a patient in a medical examination apparatus, said device comprising a support on which are mounted a television camera and a mirror sending an image of a part of the patient on to the television camera, said support being capable of being shifted with respect to the frame of the apparatus, but fixed with respect to the patient.

According to a preferred embodiment, in the case of a medical examination apparatus comprising a supporting table solidly joined to the frame of the apparatus on which a patient's bed can be shifted, the support is mounted so as to be movable in a slide rail which is solidly joined to the supporting table, and it is provided with a means for hooking to the patient's bed.

Preferably, the slide rail is a telescoping slide rail mounted in a groove made in the supporting table. This feature enables the use of the monitoring device even when the examination to be made has to be an examination of the lower part of the patient's body, and to do so without having to turn the bed over to accurately present the zone to be examined. For, the zone to be examined should always be centered in the middle of the examination tunnel: this means that the patient occupies positions, relative to the the magnet, which may vary by two meters. With this feature, the monitoring device is always precisely centered and accurate focusing is achieved since, during the examination, the monitoring device is solidly joined to the patient's bed.

According to a preferred embodiment, this solid connection between the monitoring device and the patient's bed is achieved by a contact-fastener type of hooking means.

According to another feature of the present invention, to enable the television camera to be set before the examination, said camera is fixed to the support by means of a three-point setting system. Preferably, the axis of the camera makes an angle of 45° with respect to the horizontal, with a possibility of a angular play of about 10° to 15°, thus making it possible to set the limit of the visual field of the television camera.

Furthermore, when the camera is inserted within a tunnel of magnets, it is entirely shielded to prevent any disturbance of the magnetic field.

According to another embodiment of the present invention, the mirror consists of an assembly of small, electrically insulated mirrors. The purpose of this specific construction of the mirror is to prevent any disturbance in the electromagnetic field inside the examination tunnel. Preferably, the mirror is made of metallized polycarbonate. Furthermore, the mirror makes an angle of between −0° and −15° with the horizontal, thus enabling the patient's eyes and face to be monitored properly.

Furthermore, to improve the patient's comfort, the supporting device also has a secondary mirror positioned in such a way that the patient can look out of the machine.

BRIEF DESCRIPTION OF THE DRAWINGS

Other features and advantages of the present invention will emerge from the description of a preferred embodiment, made below with reference to the appended drawings, of which.

To simplify the description, the same references are repeated for the same elements in the figures.

Moreover, the present invention has been described with reference to an apparatus for imaging by nuclear magnetic resonance. However, it is clear to those skilled in the art that the present invention can be used with other types of medical examination devices, requiring the patient to be monitored irrespective of his position in the examination apparatus.

DESCRIPTION OF A PREFERRED EMBODIMENT

Figure 1:
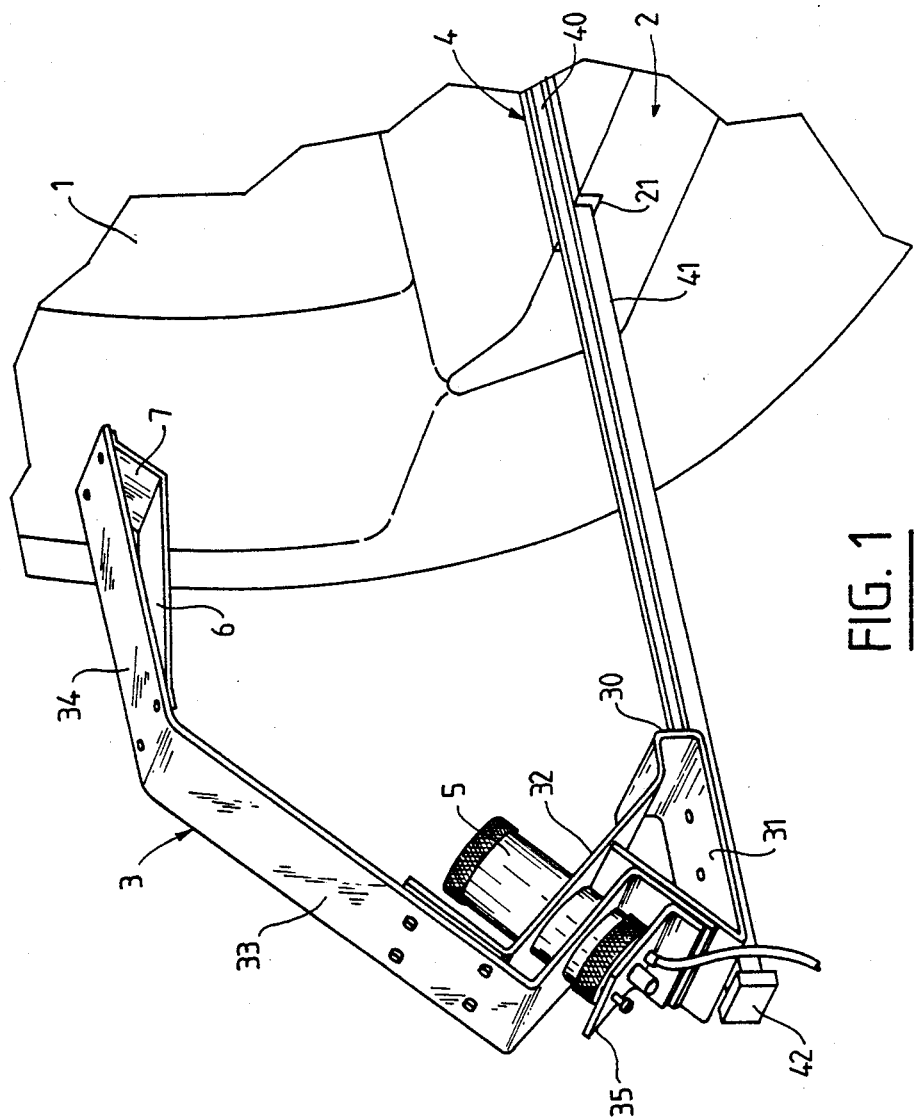
FIG. 1 shows a view in perspective of a device to monitor a patient placed in the tunnel of an apparatus for imaging by nuclear magnetic resonance.

As shown in FIG. 1, a nuclear magnetic resonance imaging apparatus essentially consists of a tunnel-shaped frame 1 designed to receive the magnets needed to create an electromagnetic field. At the lower part of the tunnel 1, there is mounted a supporting table 2. This supporting table acts, in a known way, as a guideway for the patient's bed (not shown). According to the present invention, the nuclear magnetic resonance imaging device is provided with a device to monitor the patient. This monitoring device essentially has a support 3, a television camera 5 and a mirror 6 that sends the patient's image on to the television camera. The support 3 is mounted so that it can be shifted with respect to the frame of the device, especially with respect to the supporting table 2 while, at the same time, remaining fixed with respect to the patient. To do so, the lower part of the support 3 is provided with a skid capable of sliding in a system of slide rails 4 mounted in a groove 21 made in the supporting table 2. The groove 21 is made at the center of the supporting table 2 in that part of the examining tunnel designed to receive the patient's head. The system of slide rails 4, used in the present invention, is a system of telescoping slide rails. It has a first U-shaped slide rail within which a second slide rail 41, also U-shaped, can slide. This second slide rail 41 has a central groove taking the skid of the monitoring device. The second slide rail 41 has a stopping block 42 at its end, preventing the monitoring device from being disengaged.

Figure 2:
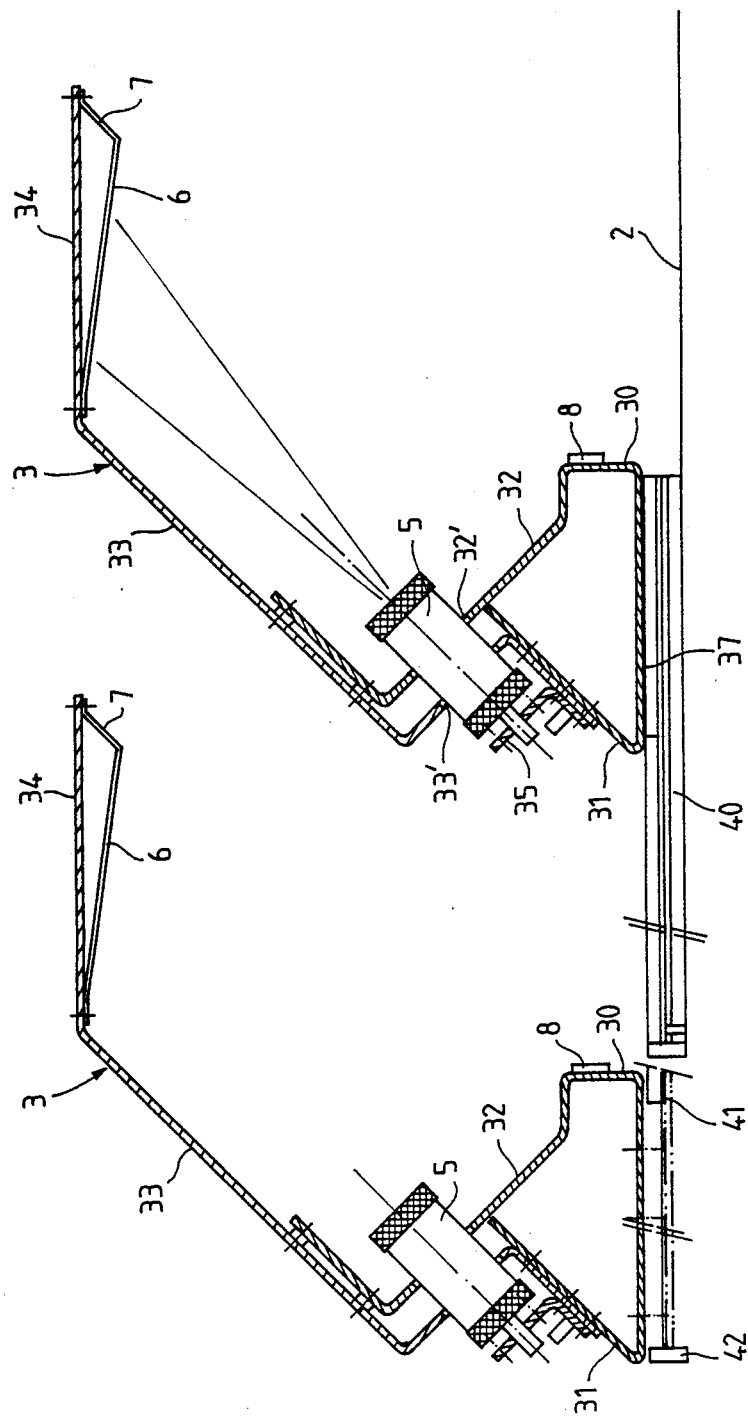
FIG. 2 shows a schematic side view of the monitoring device of FIG. 1 in two positions with respect to the supporting table.

As shown in FIGS. 1 and 2, the support 3 of the monitoring device essentially consists of a base 30. This base, made with strips of transparent, rigid plastic material such as plexiglass, has a substantially triangular shape. The side 31 of the base forms the support of the television camera, as shall be described in greater detail below. The side 32 is extended outwards by an L-shaped part which has an aperture in its middle for the television camera to pass through. Moreover, the supporting device has a substantially Z-shaped plate 33, one end of which is screwed into the side 31. The other end is extended by a substantially horizontal plate 34. The plate 34 acts as a support to the mirror 6. The mirror 6 consists of a set of small, electrically insulated mirrors made, for example, of metallized polycarbonate. This special constitution of the mirror is necessary to prevent any disturbance of the electromagnetic field inside the examination tunnel. To obtain an accurate view of the patient's face, the mirror makes an angle of between 0° and −15° with respect to the horizontal. Furthermore, to increase the patient's comfort inside the examination tunnel, the mirror 6 is extended by a secondary mirror 7 fixed between the free end of the mirror 6 and the plate 34. The mirror 7 is closed in such a way that the patient can have a view of what happens outside the examination tunnel.

As shown in FIGS. 1 and 2, the monitoring device according to the present invention has a television camera 5. This camera 5 is fixed by a three-point system to a supporting plate 35, solidly joined to the side 31 of the base. The plate 35 is substantially L-shaped. Furthermore, the television camera 5 is inserted in circular apertures made, respectively, in the side 32 and the arm 33 of the support 3. The circular apertures have a diameter which is slightly greater than that of the television camera 5 so as to enable a slight angular play. It is thus possible to set the angular deflection of the axis of the television camera to obtain a very clear view of that part of the patient which is to be monitored. Preferably, the axis of the camera forms an angle of 45° with respect to the horizontal, with a possibility of angular play ranging from 0° to 15°.

Figure 3:
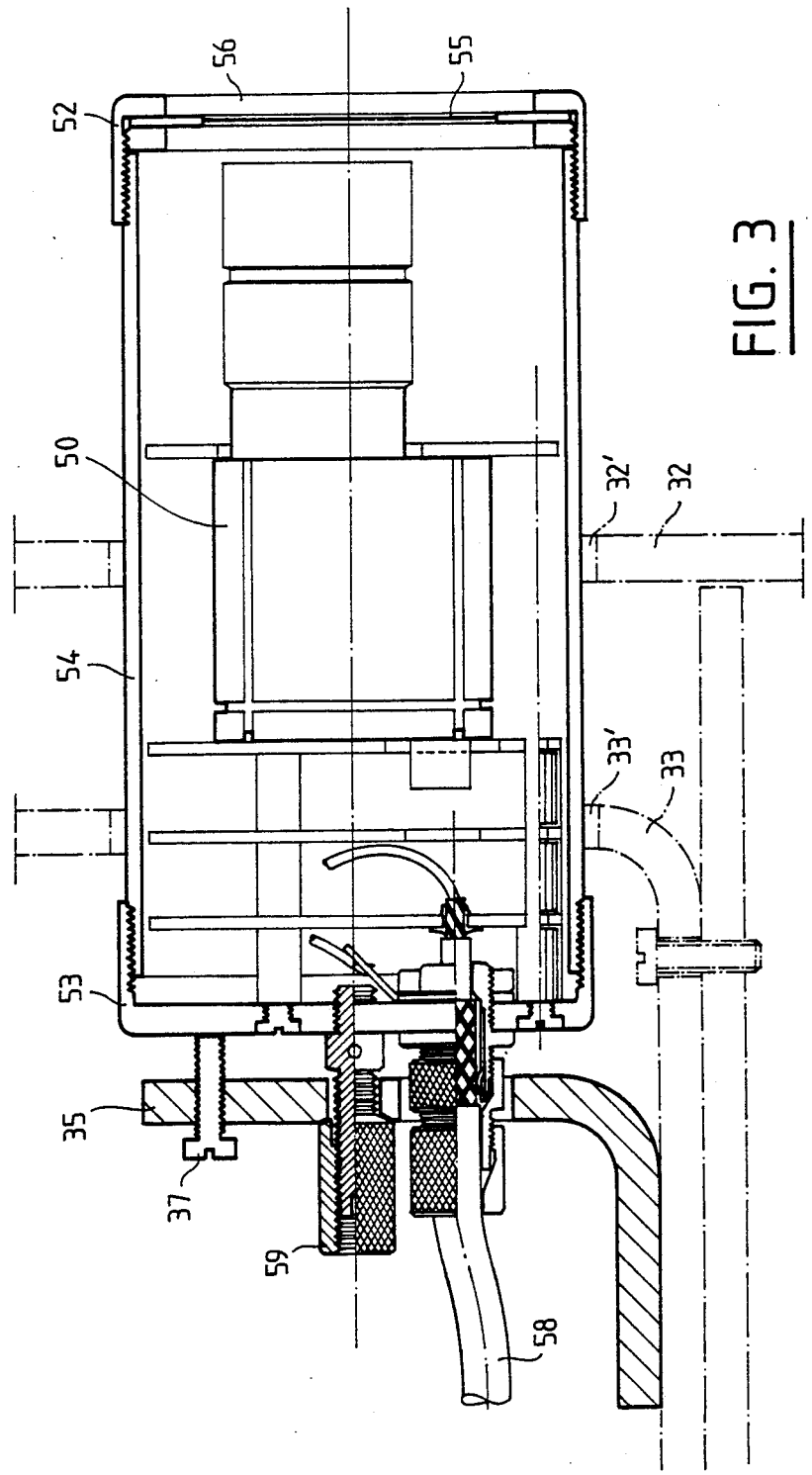
FIG. 3 shows a schematic view, in lateral elevation, of a television camera used with a monitoring device of the present invention.

As shown in FIG. 3, the television camera used with the monitoring device is an entirely shielded camera. For, a high frequency shield is needed to prevent any disturbance of the electromagnetic field. Thus, the television camera 50 is inserted in a tube 54 made of a non-magnetic material. Two caps, 52 and 53, are screwed in at each end of this tube. The cap 52, on the lens side of the camera has a central aperture 56, made of a transparent material, and is provided with a screen 55. The cap 53 has different apertures to let through the connection cables between the camera and the external processing system. In this case, the cables are formed by a triaxial cable 58, connected to the high frequency ground plane of the Faraday cage. This cable conveys the DC power supply for the television camera and the video signal emitted by this camera.

Preferably, the television camera used here is of the microcamera type with a CCD (charge coupled device) sensor capable of working without any deterioration of quality in a magnetic field of 0.5 tesla.

As shown in FIGS. 2 and 3, the camera 5 with its shielding is inserted in the two openings 32' and 33' made respectively in the side 32 and the arm 33 of the support 3. The television camera is held in position against the supporting plate 35 by means of screws 37 forming a three-point setting system enabling a slight degree of angular play in the axis of the camera. The television camera is locked into position by means of a bolt 59 screwed onto a threaded pin which is solidly joined to the shield. The bolt comes to a stop against the plate 35.

Figure 4:
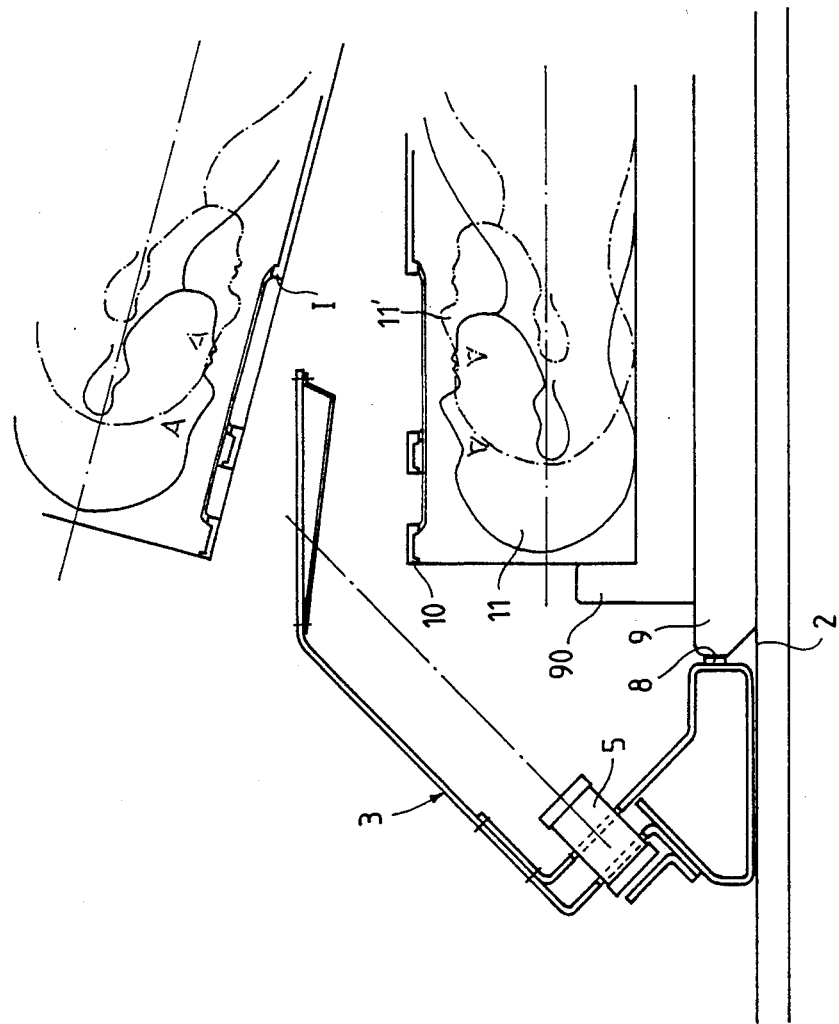
FIG. 4 shows a schematic view, in lateral elevation, explaining the functioning of the monitoring device.

Furthermore, according to the present invention, the base 30 of the monitoring device is provided with a hooking system 8 of the contact-fastening type in the embodiment shown, enabling the supporting device to be hooked to the patient's bed 9 as shown in FIG. 4.

Referring more particularly to FIG. 4, we shall now explain the operation of the monitoring device according to the present invention. During an examination, the patient is stretched out on the patient's bed 9. His head 11 lies on the head piece 90. The patient's bed is translated on the supporting table 2 and is brought to the center of the examination tunnel in a position such that the head 11 of the patient is in an examination position. In this position, the end of the bed 9, which is provided with a hooking means, can be hooked to the monitoring device by the hooking means 8. At this point of time, the monitoring device and the bed are soldily joined to each other, and any motion of the bed towards the back of the examination tunnel to enable other parts of the body to be examined will be followed by the monitoring device 3. By using a television camera with a visual axis forming an angle of 45° to the horizontal and a mirror with a dimension such that its end is substantially vertical to the patient's nose when he is correctly positioned on the head piece, a visual field of 27° is obtained, enabling accurate monitoring of the patient as shown in FIG. 4. For, in this case, the image sent on to the television camera by the mirror is the virtual image I. Even when the antenna used is a head antenna, namely when there is a blind field due to the armature 10 of the antenna, the television camera sends back an exploitable image of the patient's face. This is still true when the patient is positioned in a slightly withdrawn position with respect to the normal one, as shown by the silhouette 11' on FIG. 4. The possibility of play needed with respect to the theoretical position may be equal to plus or minus 40 mm.

The above-described monitoring device thus enables the optimum and easy monitoring of the patient inside the examination tunnel. This device also preserves perfect centering of the patient's image and optimum face-/lens/camera distance without any action by the operator, and irrespectively of the position of the patient's bed in the tunnel.

The monitoring device of the present invention enables efficient monitoring without modifying the NMR image, without any action by the operator, irrespectively of the type of the examination considered, since the patient monitoring device is solidly joined to the patient's bed.

What is claimed is:

1. A device for monitoring a patient in the tunnel of a medical examination apparatus wherein said apparatus includes a frame, said device comprising:

a support having a television camera and a mirror mounted on said support wherein said mirror sends an image of a part of the patient to the television camera;

support moving means for moving said support with respect to said frame of said apparatus wherein said support moving means is fixed with respect to said patient.

2. A device according to claim 1 wherein said medical examination apparatus includes a supporting table rigidly fixed to said frame of said apparatus, a slide rail rigidly fixed to said supporting table, a bed which is movably supported on said supporting table and wherein said support is movably mounted to said slide rail, and means for hooking said support to said patient's bed.

3. A device according to claim 2, wherein the slide rail is mounted in a groove made in the supporting table.

4. A device according to claim 1 or 2, wherein the slide is a telescoping slide.

5. A device according to claim 1 or 2, wherein the hooking means is of the contact-fastening type.

6. A device according to claim 1, wherein the camera is fixed to the support by means of a three-point setting system.

7. A device according to claim 6, wherein the axis of the camera makes an angle of 45° with the horizontal with a possibility of angular play of about 0° to 15°.

8. A device according to claim 1, wherein the camera is shielded.

9. A device according to claim 1, wherein mirror is formed by an assembly of small, electrically isolated mirrors.

10. A device according to claim 9, wherein the mirror is made with metallized polycarbonate.

11. A device according to claim 1, wherein the mirror makes an angle of 0° to −15° with the horizontal.

12. A device according to claim 1, further comprising a secondary mirror positioned to enable the patient to look outside the machine.

* * * * *

UNITED STATES PATENT AND TRADEMARK OFFICE
CERTIFICATE OF CORRECTION

PATENT NO. : 4,923,295
DATED : MAY 8, 1990
INVENTOR(S) : JACQUES SIREUL ET AL.

It is certified that error appears in the above-identified patent and that said Letters Patent is hereby corrected as shown below:

On the title page, item [75]:

In the inventors, delete "Jacob Hervé" and insert --Hervé Jacob--;

In the inventors, delete "Gauthier René" and insert --René Gauthier--.

Signed and Sealed this

Seventeenth Day of September, 1991

Attest:

HARRY F. MANBECK, JR.

Attesting Officer   Commissioner of Patents and Trademarks